US012599419B2

(12) United States Patent　　　(10) Patent No.:　US 12,599,419 B2
Tyber et al.　　　　　　　　　(45) Date of Patent:　　Apr. 14, 2026

(54) BEVELED SCREW

(71) Applicant: Tyber Medical LLC, Bethlehem, PA (US)

(72) Inventors: Jeffrey Tyber, Breinigsville, PA (US); Leo Roux, Cailure et Cuire (FR); Yoann Tymans, Myzieu (FR)

(73) Assignee: Tyber Medical LLC, Bethlehem, PA (US)

( * ) Notice: Subject to any disclaimer, the term of this patent is extended or adjusted under 35 U.S.C. 154(b) by 0 days.

(21) Appl. No.: 18/935,917

(22) Filed: Nov. 4, 2024

(65) Prior Publication Data

US 2025/0057575 A1　　Feb. 20, 2025

Related U.S. Application Data

(63) Continuation-in-part of application No. 17/829,429, filed on Jun. 1, 2022, now Pat. No. 12,144,531, which is a continuation of application No. 17/108,168, filed on Dec. 1, 2020, now Pat. No. 11,389,221, which is a continuation of application No. 16/201,144, filed on Nov. 27, 2018, now Pat. No. 10,888,365, which is a continuation-in-part of application No. 15/646,497, filed on Jul. 11, 2017, now Pat. No. 10,383,737, which is a continuation-in-part of application No. 15/213,935, filed on Jul. 19, 2016, now Pat. No. 10,058,431, which is a continuation-in-part of application No. 15/162,657, filed on May 24, 2016, (Continued)

(51) Int. Cl.
　　*A61B 17/86*　　(2006.01)
　　*A61B 17/68*　　(2006.01)

*A61F 2/46*　　(2006.01)
　　*A61B 17/56*　　(2006.01)
　　*A61B 17/88*　　(2006.01)

(52) U.S. Cl.
　　CPC .......... *A61B 17/8605* (2013.01); *A61B 17/68* (2013.01); *A61B 17/86* (2013.01); *A61B 17/8645* (2013.01); *A61F 2/4606* (2013.01); *A61B 2017/565* (2013.01); *A61B 17/863* (2013.01); *A61B 17/8875* (2013.01)

(58) Field of Classification Search
　　CPC ........ A61B 7/86; A61B 7/8605; A61B 7/8645
　　See application file for complete search history.

(56) References Cited

U.S. PATENT DOCUMENTS 4,537,185　A　　8/1985　Stednitz
6,953,463　B2 *　10/2005　West, Jr. ............... A61F 2/0811
　　　　　　　　　　　　　　　　　　　606/326

(Continued)

FOREIGN PATENT DOCUMENTS

WO　　WO 2022/271504　　12/2022

OTHER PUBLICATIONS

PCT/US2024/046060 International Search Report and Written Opinion mailed Dec. 17, 2024.

*Primary Examiner* — Larry E Waggle, Jr.
(74) *Attorney, Agent, or Firm* — Joseph E. Maenner; Maenner & Associates, LLC

(57)　　　　　ABSTRACT

A screw includes a screw head having a bevel and an elongate shaft attached to the screw head. The shaft has a central longitudinal axis. A tip is attached to the shaft, distal from the head. A method in implanting the screw into a bone or bone fragment is also disclosed.

13 Claims, 3 Drawing Sheets

Related U.S. Application Data now Pat. No. 10,369,251, which is a continuation-in-part of application No. 14/948,322, filed on Nov. 22, 2015, now Pat. No. 10,201,433, which is a continuation-in-part of application No. 14/513,300, filed on Oct. 14, 2014, now Pat. No. 10,864,081, which is a continuation-in-part of application No. 14/054,100, filed on Oct. 15, 2013, now Pat. No. 9,387,087.

(60) Provisional application No. 61/715,891, filed on Oct. 19, 2012.

(56)     References Cited

U.S. PATENT DOCUMENTS

| | | | |
|---|---|---|---|
| 7,083,647 B1 * | 8/2006 | Sklar | A61F 2/0811 |
| | | | 623/13.14 |
| 9,289,220 B2 * | 3/2016 | Wolfe | A61B 17/1775 |
| 10,898,248 B2 * | 1/2021 | Cundiff | A61F 2/30 |
| 11,045,239 B2 * | 6/2021 | Blitz | A61B 17/8605 |
| 11,672,570 B2 * | 6/2023 | Stuart | A61B 17/7055 |
| | | | 606/279 |
| 2019/0388131 A1 | 12/2019 | Mehl et al. | |
| 2020/0093525 A1 | 3/2020 | Zastrozna | |
| 2021/0282822 A1 | 9/2021 | Conley | |
| 2022/0313328 A1 * | 10/2022 | Korman | A61B 17/8891 |

* cited by examiner

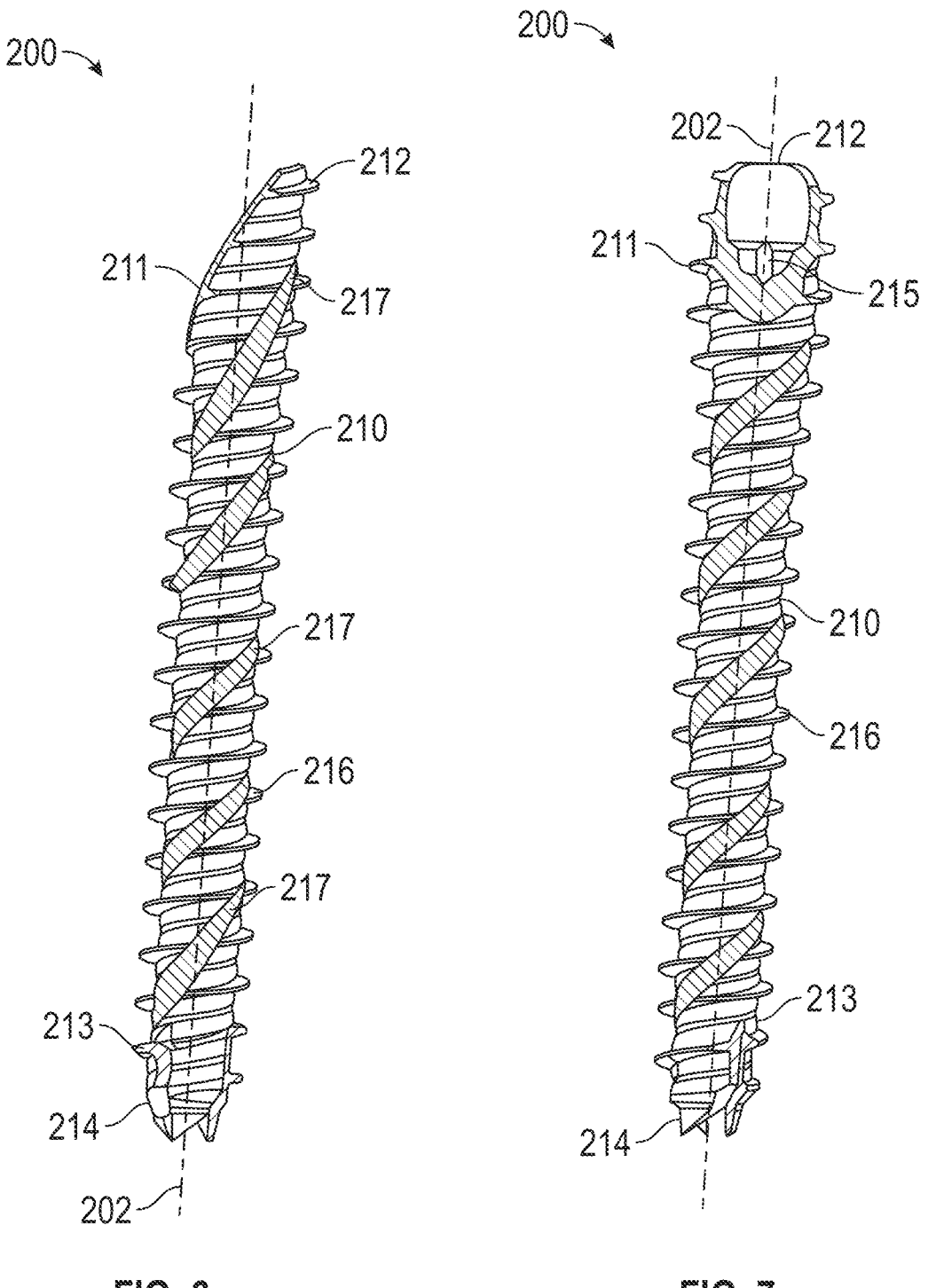
FIG. 6          FIG. 7

BEVELED SCREW

CROSS-REFERENCE TO RELATED APPLICATIONS

The present application is a continuation-in-part of U.S. application Ser. No. 17/829,429, filed on Jun. 1, 2022 and issued on Nov. 19, 2024 as U.S. Pat. No. 12,144,531, which is a continuation of application Ser. No. 17/108,168, filed on Dec. 1, 2020 and issued on Jul. 19, 2022 as U.S. Pat. No. 11,389,221, which is a continuation of application Ser. No. 16/201,144, filed on Nov. 27, 2018 and issued on Jan. 12, 2021 as U.S. Pat. No. 10,888,365, which is a continuation-in-part of application Ser. No. 15/646,497, filed on Jul. 11, 2017 and issued on Aug. 20, 2019 as U.S. Pat. No. 10,383, 737, which is a continuation-in-part of application Ser. No. 15/213,935, filed on Jul. 19, 2016 and issued on Aug. 28, 2018 as U.S. Pat. No. 10,058,431, which is a continuation-in-art of application Ser. No. 15/162,657, filed on May 24, 2016 and issued on Aug. 6, 2019 as U.S. Pat. No. 10,369, 251, which is a continuation-in-part of application Ser. No. 14/948,322, filed on Nov. 22, 2015 and issued on Feb. 12, 2019 as U.S. Pat. No. 10,201,433, which is a continuation-in-part of application Ser. No. 14/513,300, filed on Oct. 14, 2014 and issued on Dec. 15, 2020 as U.S. Pat. No. 10,864, 081, which is a continuation-in-part application of U.S. patent application Ser. No. 14/054,100, filed on Oct. 15, 2013 and issued on Jul. 12, 2016 as U.S. Pat. No. 9,387,087, which claims priority from U.S. Provisional Patent Application Ser. No. 61/715,891, filed on Oct. 19, 2012, all of which are incorporated by reference herein in their entireties.

FIELD OF THE INVENTION

The invention relates to screws that can be used with a beveled head to reduce or eliminate the head protruding above the bone into which the screw is inserted, thereby reducing skin tears and infections.

DESCRIPTION OF THE RELATED ART

Screws can be implanted into bone to repair broken bones. Different screws are used depending on the location of the break, the severity of the break, and the bone(s) that is/are being repaired.

It can be advantageous to angle the screw at an oblique angle relative to the axis of the bone to obtain proper connection between adjacent bones or bone fragments. This, however, can result in at least a part of the screw head extending above the bone, which can lead to undesired bumps along the bone surface and the potential for the screw head to tear into the skin, possibly resulting in infection.

It would be beneficial to provide a screw that extends outside of the bone as little as possible and also provides a rounded surface to reduce unwanted bumps and potential skin tear sites.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a screw that includes a screw head having a bevel and an elongate shaft attached to the screw head. The shaft has a central longitudinal axis. A tip is attached to the shaft, distal from the head. A method in implanting the screw into a bone or bone fragment is also disclosed.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 6 is a side elevational view of an alternative embodiment of a screw according to the present invention; and FIG. 7 is a front elevational view of the screw of FIG. 6.

DETAILED DESCRIPTION

Figure 3:
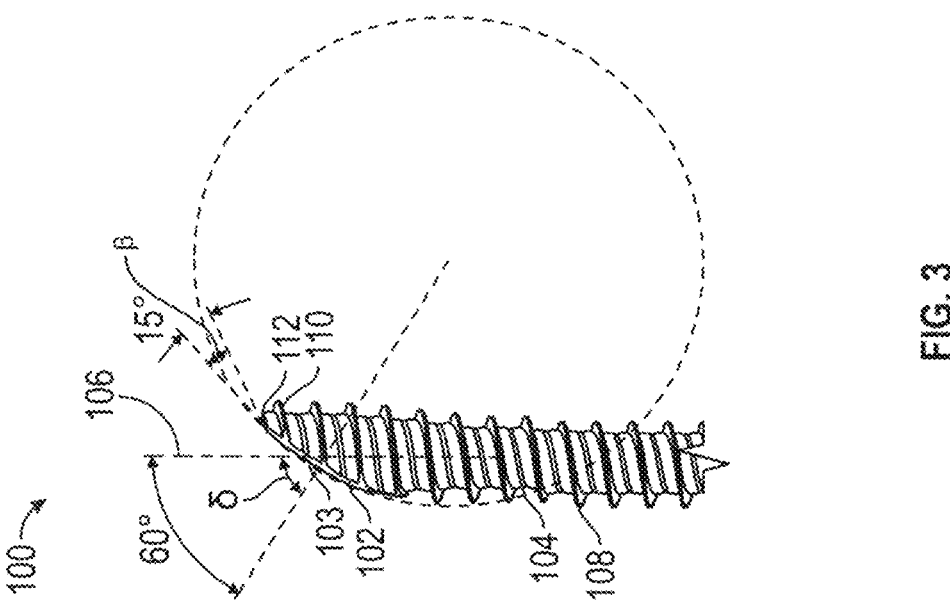
FIG. 3 is an enlarged side elevational view of the top portion of the screw of FIG. 1.
Figure 2:
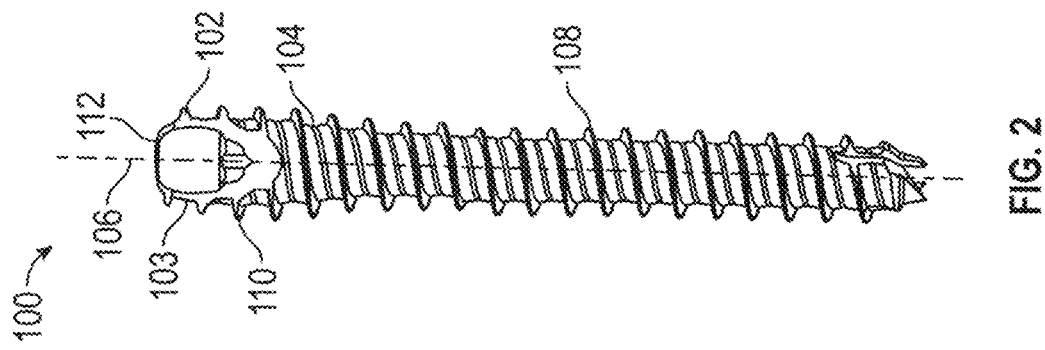
FIG. 2 is a front elevational view of the screw of FIG. 1.
Figure 1:
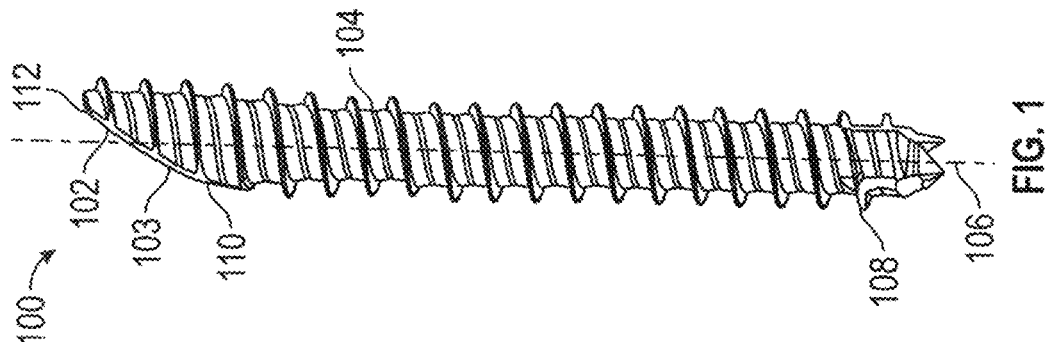
FIG. 1 is a side elevational view of an exemplary embodiment of a beveled screw according to the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

The word "about" is used herein to include a value of +/−10 percent of the numerical value modified by the word "about" and the word "generally" is used herein to mean "without regard to particulars or exceptions."

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to the Figures, a beveled screw 100 according to an exemplary embodiment of the present invention is shown. Screw 100 includes a screw head 102 with a bevel 103. Screw head 102 is attached to an elongate shaft 104 having a central longitudinal axis 106. Screw head 102 includes threads 108 and, as can be seen in FIGS. 1-4, a top end 110 of thread 108 terminates at bevel 103. Thread 108 can be continuous or, alternatively, thread 108 can be discontinuous around head 102.

Screw head 102 forms a dome shape in a plane extending along the line defining bone surface 52 and extending perpendicularly from the plane of the paper. Screw head 102 is not beveled with a straight cut, but instead arcs with a constant radius of curvature, forming the dome shape. In an exemplary embodiment, the radius can be between about 5 mm and about 15 mm.

A trailing, or proximal end 112 of head 102 spans an arc of about 15 degrees to minimize or eliminate proximal end 112 of head 102 extending outwardly from bone 50 after implantation.

Figure 5:
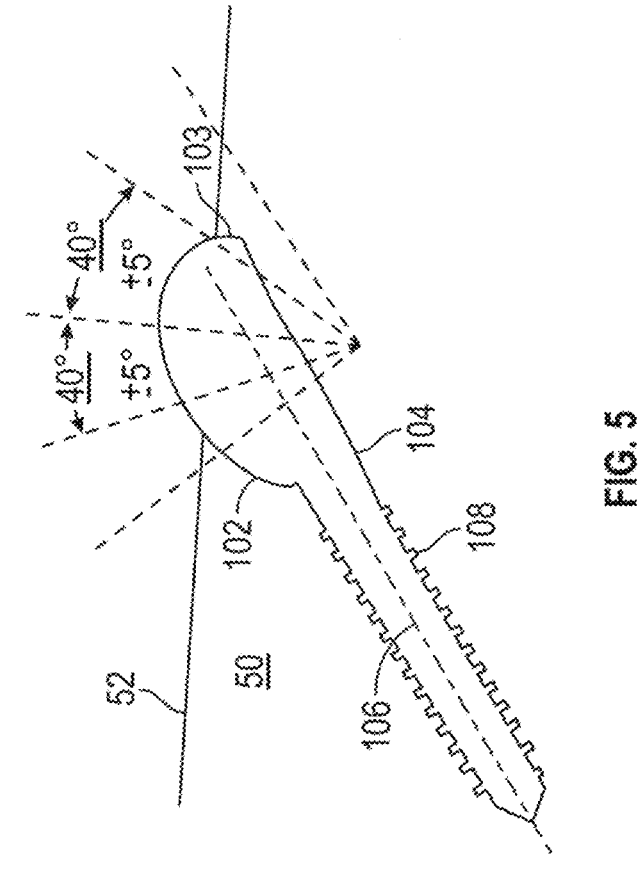
FIG. 5 is a sectional view of the screw of FIG. 1 implanted into a bone.
Figure 4:
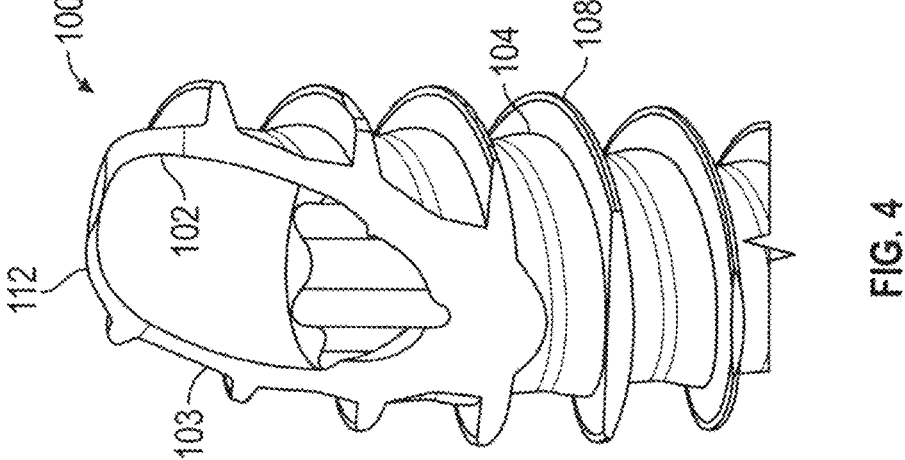
FIG. 4 is an enlarged perspective view of the head of the screw of FIG. 1.

Because screw head 102 is dome-shaped, screw head 102 is also elliptical in shape and gives the surgeon a little bit of wiggle room so if the insertion angle is not perfect, screw head 102 will still have a smooth transition at implantation. The present design makes the elliptical shape larger and more forgiving to allow the surgeon to focus on where the distal end of the screw 100 needs to be without worrying too much about the proximal end (screw head 102) being smooth/flush with bone surface 52 of bone 50. As shown in FIG. 5, the screw 100 anticipates an insertion angle of 40 degrees from the surface, with a tolerance of about +5 degrees so that the screw 100 is more forgiving for different anatomies. While the anticipated insertion angle is 40 degrees, those skilled in the art will recognize that modifications to screw head 102 for insertion angles different from 40 degrees are also contemplated in this application.

This specified angle ensures the rounded screw head 102 will be flush with the bone surface 52 after implantation, providing a smooth transition to prevent or reduce skin irritation.

Referring specifically to FIG. 3, angle δ is the axis of revolution that forms the dome shape and angle β is the resultant of this dome from its center to its ends. Angle β allows screw 100 to follow an erroneous trajectory without allowing sharp edges of screw 100 to protrude from the bone. In an exemplary embodiment, angle δ can be about 60 degrees +/−5 degrees and angle β can be 15 degrees +/−5 degrees.

Screw 100 can be a fully threaded screw, as shown in FIGS. 1-5. Alternatively, screw 100 can be a compressive screw with threads that extend only part way from head 102 and part way from the tip, with central part of shaft 104 being threadless.

Referring now to FIGS. 6 and 7, a screw 200 according to the present invention is shown. Screw 200 includes an elongate shaft 210 having a proximal end 212 and a distal end 214, and a central longitudinal axis 202 extending between the proximal end 212 and the distal end 214. Shaft 210 can be fully cannulated, with a cannulation 215 extending along the longitudinal axis between the proximal end 212 and the distal end 214. Cannulation 215 in shaft 210 is sized to allow a guide wire (not shown) to extend therethrough. By way of example only, screw 200 can be provided in various lengths, depending on the required usage, and can extend between about 40 mm and about 70 mm in length.

Shaft 210 has a proximal portion 211 and a distal portion 213. Shaft 210 includes a plurality of flutes 217 formed along an exterior of shaft 210 within proximal portion 211. In an exemplary embodiment, three flutes 217 extend the length of shaft 210. Flutes 217 are evenly spaced 120 degrees apart from each other around the exterior of shaft 210 and extend helically around shaft 210. Flutes 217 are provided to reduce the insertion torque. The proximal portion 211 of shaft 210 can have a larger diameter than distal portion 213, therefore the torque will start to increase due to friction as screw 200 is advanced into bone. This increased torque can cause the bone to start to rotate or could break a screwdriver or screw 200. The flutes 217 are tapping the bone to reduce that torque. Flutes 217 extend from proximal end 212 to distal end 214 of shaft 210.

A thread 216 extends along the shaft 210. In an exemplary embodiment, only a single thread 216 is provided. Those skilled in the art, however, will recognize that more than a single thread 216 can be provided. Thread 216 is broken at each flute 217, but continues across flute 217 as if flute 217 was not present and thread 216 was continuous.

It will be further understood that various changes in the details, materials, and arrangements of the parts which have been described and illustrated in order to explain the nature of this invention may be made by those skilled in the art without departing from the scope of the invention as expressed in the following claims.

We claim:
1. A screw comprising:
   a screw head having a bevel, wherein the bevel forms a dome shape;
   an elongate shaft attached to the screw head, the shaft having a central longitudinal axis and a cannula extending along the longitudinal axis; and a tip attached to the shaft, distal from the head,
    wherein the screw head and the shaft are solid around the
        cannula, and
    wherein the screw is fully threaded.

2. The screw according to claim 1, wherein a top end of the thread terminates at the bevel.

3. The screw according to claim 1, wherein the thread is continuous around the screw head.

4. The screw according to claim 1, wherein the screw head arcs with a constant radius of curvature, forming the dome shape.

5. The screw according to claim 4, wherein the radius is between about 5 mm and about 15 mm.

6. The screw according to claim 1, wherein the head comprises a trailing end.

7. The screw according to claim 6, wherein the trailing end spans an arc of about 15 degrees.

8. The screw according to claim 1, wherein the screw head is elliptical in shape.

9. The screw according to claim 1, wherein the screw anticipates an insertion angle of 40 degrees.

10. The screw according to claim 1, further comprising a plurality of flutes formed along an exterior of the shaft.

11. The screw according to claim 10, wherein the flutes extend the length of the shaft.

12. The screw according to claim 10, wherein three flutes are evenly spaced 120 degrees apart from each other around the exterior of the shaft.

13. The screw according to claim 10, wherein the flutes extend helically around the shaft.

* * * * *